US00PP20484P2

(12) United States Plant Patent
Robb

(10) Patent No.: US PP20,484 P2
(45) Date of Patent: Nov. 17, 2009

(54) ***VINCA MINOR* PLANT NAMED 'PARVIN'**

(50) Latin Name: *Vinca minor*
Varietal Denomination: Parvin

(75) Inventor: John Robb, Kulnurra (AU)

(73) Assignee: The Paradise Seed Company Pty. Ltd., Kulnurra (AU)

( * ) Notice: Subject to any disclaimer, the term of this patent is extended or adjusted under 35 U.S.C. 154(b) by 0 days.

(21) Appl. No.: 12/286,977

(22) Filed: Oct. 4, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Susan B Mccormick Ewoldt
(74) *Attorney, Agent, or Firm*—Mark P. Bourgeois

(57) ABSTRACT

A new and distinct cultivar of *Vinca minor* plant named 'Parvin' characterized by variegated leaves having a dark green center surrounded by yellow-white margins and semi-double violet flowers.

1 Drawing Sheet

Botanical classification: *Vinca minor.*
Variety denomination: 'Parvin'.

BACKGROUND OF THE INVENTION

The present Invention relates to a new and distinct cultivar of *Vinca minor* plant, botanically known as *Vinca minor*, and hereinafter referred to by the name 'Parvin'. The new cultivar was discovered and selected in the inventor's outdoor garden in a cultivated area of Kulnurra, NSW Australia in 2000. 'Parvin' was discovered as a naturally occurring branch sport of an unnamed *Vinca minor* cultivar.

The first asexual propagation of 'Parvin' was done by the inventor in Kulnurra, NSW Australia using a semi-mature tip cutting in late 2000. The new cultivar has subsequently been propagated by stem cuttings and has remained stable and true to type in successive generations of asexual reproduction.

SUMMARY OF THE INVENTION

The following traits have been repeatedly observed and are determined to be the unique characteristics of 'Parvin'. These characteristics in combination distinguish 'Parvin' as a new and distinct cultivar:

1. Variegated leaves having a dark green center surrounded by yellow-white margins.
2. Semi-double violet flowers.

The closest comparison cultivar is the unnamed parent plant. *Vinca minor* 'Parvin' is different from the unnamed parent plant in having variegated leaves having a dark green center surrounded by yellow-white margins. The leaves of the parent plant are dark green.

'Parvin' can be compared to other commercially available variegated cultivars of *Vinca minor* such as 'Golden' (not patented), 'Blue and Gold' (not patented), 'Ralph Shugert' (U.S. Plant Pat. No. PP6,960) and 'Sunny Skies' (U.S. Plant Pat. No. PP13,466).

The new cultivar 'Parvin' is distinguishable from 'Golden' by the following characteristics:

1. 'Parvin' has leaves with wider margins than 'Golden'.
2. 'Parvin' has lighter color margins than 'Golden'.

The new cultivar 'Parvin' is distinguishable from 'Blue and Gold' by the following characteristics:

1. 'Parvin' has leaves with wider margins than 'Blue and Gold'.
2. 'Parvin' has lighter color margins than 'Blue and Gold'.

The new cultivar 'Parvin' is distinguishable from 'Ralph Shugert' by the following characteristics:

1. 'Parvin' has leaves with a darker green center than 'Ralph Shugert'.
2. 'Parvin' has leaves with yellow-white colored margins. The margins of 'Ralph Shugert' are white.

The new cultivar 'Parvin' is distinguishable from 'Sunny Skies' by the following characteristics:

1. 'Parvin' has leaves with lighter color margins than 'Sunny Skies'.

BRIEF DESCRIPTION OF THE PHOTOGRAPH

The accompanying photograph illustrates the distinguishing traits of *Vinca minor* 'Parvin'.

The top photograph is an overall view of a 12 month old plant.

The bottom photograph is a close up view of the flowers and leaves.

The photographs were taken using conventional techniques and although colors may appear different from actual colors due to light reflectance it is as accurate as possible by conventional photographic techniques.

DETAILED BOTANICAL DESCRIPTION

The new *Vinca minor* has not been observed under all possible environmental conditions. The phenotype may vary somewhat with variations in environment such as temperature and light intensity, without, however, any variance in genotype. The following is a detailed description of the new *Vinca minor* cultivar named 'Parvin'. Data was collected in Melbourne, Australia from 12 month old plants grown in 6 inch diameter containers under both greenhouse and open field conditions. In the following description, color references are made to The Royal Horticultural Society Colour Chart, 1995 Edition.

Botanical classification: *Vinca minor* cultivar 'Parvin'.

Parentage: 'Parvin' is a naturally occurring branch sport of an unnamed *Vinca minor* cultivar.

Propagation: Layering or stem cuttings (leaf and node).
Root description: Fine and fibrous.
Commercial classification: Lesser Periwinkle
Type: Hardy, evergreen, creeping vine. Grown as a ground-cover.
Hardiness: Plants have survived temperature of −29.degrees F. Hardy in Zones 4–9.
Vigor: Grows readily in sun and shade and soils of reasonable fertility and moisture. The best coloration is observed when grown in the shade or part shade in moist, but well-drained soil; excessive sunlight may wash-out the color or scorch the leaves.
Plant description:
*Growth habit.*—Prostrate, creeping. Stems arise vertically from the crown and may stay erect and reach a height of 15–20 cm. but they typically elongate into a vine of indeterminate length. The vine stems become prostrate as they elongate and form infrequent branches.
*Bloom season.*—Blooms in mid-late spring and sporadically later in the season.
*Disease resistance/susceptibility.*—No known disease problems have been observed.
*Stems.*—Round, diameter 1–2 mm., green, rarely branched.
*Internodes.*—2.5–3 cm.
Foliage:
*Margin.*—Entire.
*Shape.*—Ovate.
*Arrangement.*—Opposite.
*Leaf dimension.*—1.5 to 4.0 cm. in length, 1.0 to 2.0 cm. in width.
*Attitude.*—Slightly curved, leaf blades are concave.
*Apex.*—Acute.
*Base.*—Obtuse.
*Petiole.*—Present, very short 3–4 mm.
*Venation.*—Prominent midrib and secondary veins, pale green color.
*Leaf color.*—Emerging leaves have green centers (137A), that is maintained to maturity. The center color typically occupies from 75 to 85% of the total leaf surface. Some leaves have an irregular, intermediary color (Grey-green 190B) between the green centre and the yellow-white margin, this is not on all leaves. The margins are a yellow-white color (158A) throughout maturation.
Flowers:
*Flowers.*—Semi-double, violet 200A.
*Type.*—Salverform, solitary.
*Flower dimensions.*—2 to 3 cm. in diameter, 1–2 cm. in depth.
*Corolla.*—Violet-blue (93B–C), 2–3 layers of petals, irregular, overlapping. Lobes are 1.0–1.5 cm. in length, 0.5 cm. to 1.2 cm. at tip in width, orifice 5 mm.
*Fruit/seeds.*—Fruit and seeds have not been observed.
*Disease and pest resistance.*—Disease and pest resistance has not been observed.

The invention claimed is:

1. A new and distinct variety of *Vinca minor* plant named Parvin, as described and illustrated.

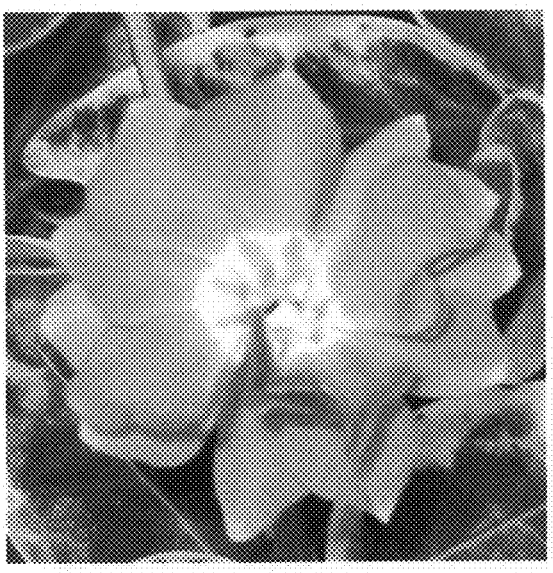
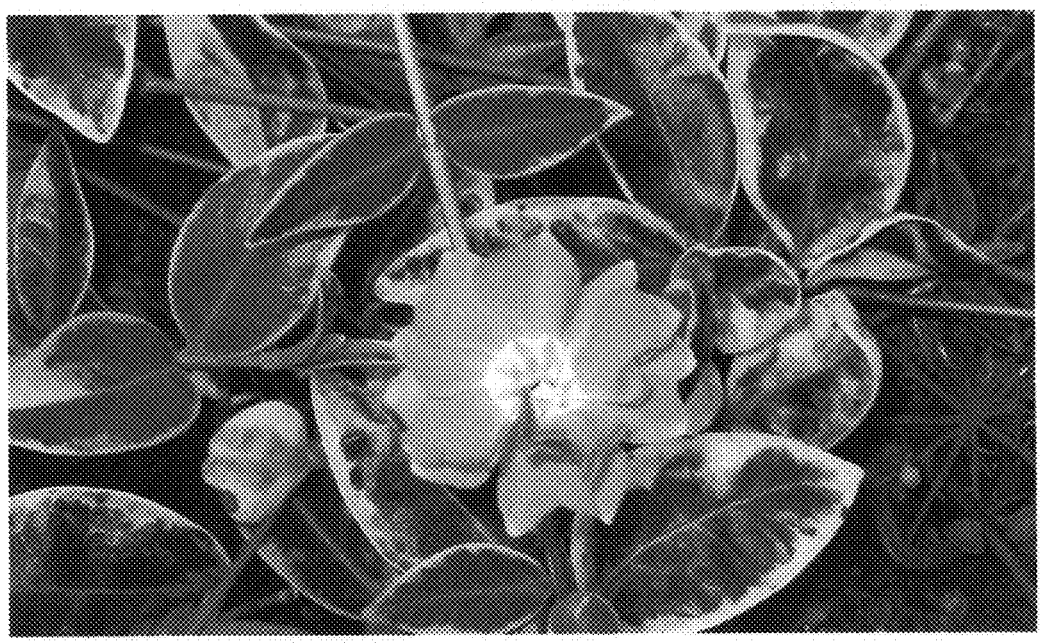

* * * * *